(12) United States Patent
Drillio

(10) Patent No.: US 9,192,502 B2
(45) Date of Patent: Nov. 24, 2015

(54) ANKLE-FOOT ORTHOTIC

(71) Applicant: Robert C. Drillio, Scituate, MA (US)

(72) Inventor: Robert C. Drillio, Scituate, MA (US)

(*) Notice: Subject to any disclaimer, the term of this patent is extended or adjusted under 35 U.S.C. 154(b) by 196 days.

(21) Appl. No.: 13/972,663

(22) Filed: Aug. 21, 2013

(65) Prior Publication Data
US 2014/0066829 A1    Mar. 6, 2014

Related U.S. Application Data

(60) Provisional application No. 61/691,453, filed on Aug. 21, 2012.

(51) Int. Cl.
*A61F 5/00* (2006.01)
*A61F 5/01* (2006.01)

(52) U.S. Cl.
CPC ................. *A61F 5/0127* (2013.01)

(58) Field of Classification Search
CPC ............. A61F 2002/503; A61F 2002/701; A61F 2002/704; A61F 2002/7625; A61F 2002/7645; A61F 2/68; A61F 2002/5003; A61F 5/0127; A61F 2002/7635; A61F 2/60; A61F 2/6607; A61F 2002/5007; A61F 2005/0167; A61F 2005/0169; A61F 2005/0179; A61F 5/0013; A61F 5/0111; A61F 2005/0134; A61F 2005/0165; A61F 5/0102; A61F 2005/0148; A61F 2005/0158; A61F 5/0125

USPC ............... 602/23–28; 128/882; 5/624
See application file for complete search history.

(56) References Cited

U.S. PATENT DOCUMENTS

| | | | | |
|---|---|---|---|---|
| 4,934,355 A * | 6/1990 | Porcelli | | 602/16 |
| 5,328,444 A * | 7/1994 | Whiteside | | 602/16 |
| 7,018,350 B2 * | 3/2006 | Hinshon | | 602/16 |
| 8,221,341 B1 * | 7/2012 | Al-Oboudi | | 602/27 |
| 2005/0148914 A1 * | 7/2005 | Currier | | 602/5 |

* cited by examiner

*Primary Examiner* — Michael Brown
(74) *Attorney, Agent, or Firm* — Kriegsman & Kriegsman

(57) ABSTRACT

An ankle-foot orthotic device is designed to closely simulate the natural movement of a lower extremity throughout a proper walking gait cycle. The orthotic device includes upper and lower support members that are pivotally coupled by opposing dorsiflexion assist members. The lower support member includes a rigid, unitary cup for receiving the heel and ankle portions of the lower extremity. The cup is shaped to include a continuous slot that allows for at least 5 degrees of compression upon initial heel strike and thereby promotes a smooth, decelerating heel roll. The lower support member additionally includes a rigid footplate on which is mounted a flexible overlay, the overlay extending beyond the footplate in the medial aspect to promote proper pronation into mid-stance. A compressible stop is mounted on the lower support member and selectively contacts the upper support member to prevent hyperextension of the lower extremity.

4 Claims, 10 Drawing Sheets

ANKLE-FOOT ORTHOTIC

FIELD OF THE INVENTION

The present invention relates generally to orthotic devices and more particularly to orthotics for the ankle and foot.

BACKGROUND OF THE INVENTION

An ankle-foot orthosis (also commonly referred to in the art simply as an AFO) is an orthotic device that firmly surrounds at least a portion of the ankle and foot of a patient. An ankle-foot orthosis is commonly constructed as a relatively lightweight and rigid brace that supports the lower leg and foot of a patient and serves to, among other things, properly control the position and motion of the ankle and foot of the patient through each gait cycle, compensate for muscular weakness and/or correct deformities. For this reason, ankle-foot orthotic devices are commonly utilized in the treatment of patients suffering from a wide variety of muscular disorders, such as stroke patients.

One type of ankle-foot orthosis which is well known in the art is constructed as a rigid brace which utilizes a solid ankle design. In other words, the brace includes an enlarged, solid piece of rigid material, such as polypropylene, that wraps around the majority of the foot, ankle and lower leg of the patient. Although useful in providing the patient with the requisite degree of stabilization for adequate weight support, ankle-foot orthotics that rely on a unitary, solid design inherently lack the flexibility to assist the patient to closely simulate the proper gait cycle.

Specifically, a proper gait cycle consists of the events from first heel strike (i.e., contact of the heel onto the ground) to second heel strike on the same foot. In the industry, the gait cycle is commonly separated into two principal phases: (1) the stance phase—the weight bearing portion of the gait cycle (i.e., the period of direct contact of the foot against the ground), and (2) the swing phase—the non-weight bearing portion of the gait cycle (i.e., the period in which the foot swings above the ground, from toe-off to subsequent heel strike). As can be appreciated, 62% of gait is weight-bearing, whereas 38% of gait is non-weight bearing. Accordingly, it is to be understood that proper lower extremity support is essential to a patient with physical limitations.

The stance phase of the proper walking gait cycle includes five defined stages: (1) initial contact—when the heel of the patient first strikes the ground (i.e., initial heel strike), (2) loading response—the period from when weight bears on the loaded extremity after initial contact until the opposite foot is lifted for the swing phase, (3) mid stance—the first half of single limb support from when the opposite foot is lifted until weight is disposed over the fore foot, (4) terminal stance—the period from when heel rises until the opposite foot strikes the ground, and (5) pre swing—the period from when the initial contact of the opposite foot to toe-off on the first foot.

It is to be understood that the lower extremity of a patient includes three natural rockers to assist in the complex kinetic chain required to perform the stance phase. Specifically, the lower extremity includes (1) a heel rocker that acts as a fulcrum as the foot rolls into plantar flexion by allowing the limb to roll forward as body weight is dropped thereon after the initial strike, with pre-tibial muscles decelerating the foot drop and drawing the proximal end of the tibia forward, (2) an ankle rocker that acts as a fulcrum as the tibia moves forward relative to the foot once the forefoot strikes the ground, with tibia progression controlled by eccentric contraction of the soleus muscle in the back part of the lower leg, and (3) a forefoot rocker that acts as a fulcrum as tibial progression advances to toe-off (i.e., as the heel rises, the fulcrum for the tibia as advancement shifts to the metatarsal heads, with progression accelerated as body weight falls beyond the area of foot support).

As referenced briefly above, it is often desirable for an ankle-foot orthosis to closely simulate the proper motion of the treated lower extremity throughout the gait cycle. Because the gait cycle requires a relatively complex kinetic chain of movement in the lower extremity, the majority of which is load-bearing, it is often important that an ankle-foot orthosis be designed to promote the proper sequence of complex movement.

In particular, it has been found that the heel strike is a traumatic event that creates substantial amount of shock, or force, in the heel. However, traditional AFOs that rely upon a solid design fail, among other things, to properly decelerate the heel upon initial heel strike to create a smooth roll and thereby simulate proper movement of the heel rocker. Rather, solid ankle design AFOs tend to throw the weight of the patient forward and/or outward in a rapid manner and without proper control, which is highly undesirable.

SUMMARY OF THE INVENTION

It is an object of the present invention to provide a new and improved orthotic device.

It is another object of the present invention to provide a new and improved orthotic device that is designed to support the ankle and foot of a patient.

It is yet another object of the present invention to provide an orthotic device as described above that enables the treated ankle and foot to closely simulate the natural movement of a lower extremity throughout a proper walking gait cycle.

It is yet still another object of the present invention to provide an orthotic device as described above that is specifically designed to allow for attenuation of the initial heel strike force (i.e., to simulate the proper absorption of force onto the heel over an extended period of time to minimize the risk of injury).

It is even still another object of the present invention to provide an orthotic device as described above that is designed to allow for adequate deceleration, or rocking, of the foot from initial heel strike to throughout the stance phase as weight transfers from the treated extremity to the other extremity.

It is another object of the present invention to provide an orthotic device as described above that includes a limited number of parts, that is inexpensive to manufacture and that is easy to use. Accordingly, as a principal feature of the present invention, there is provided an orthotic for treating a lower extremity of a patient, the lower extremity comprising a tibial portion, an ankle portion, a heel portion and a foot portion, the orthotic comprising (a) an upper support member adapted to conform to the tibial portion, (b) a lower support member adapted to conform to the foot, heel and ankle of the patient, the lower support member being pivotally coupled to the upper support member, (c) wherein the lower support member comprises a rigid cup for receiving the heel and ankle portions of the lower extremity, the cup being shaped to define a slot that enables the cup to compress upon the application of a suitable compressive force thereto.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE INVENTION

Figure 1A:
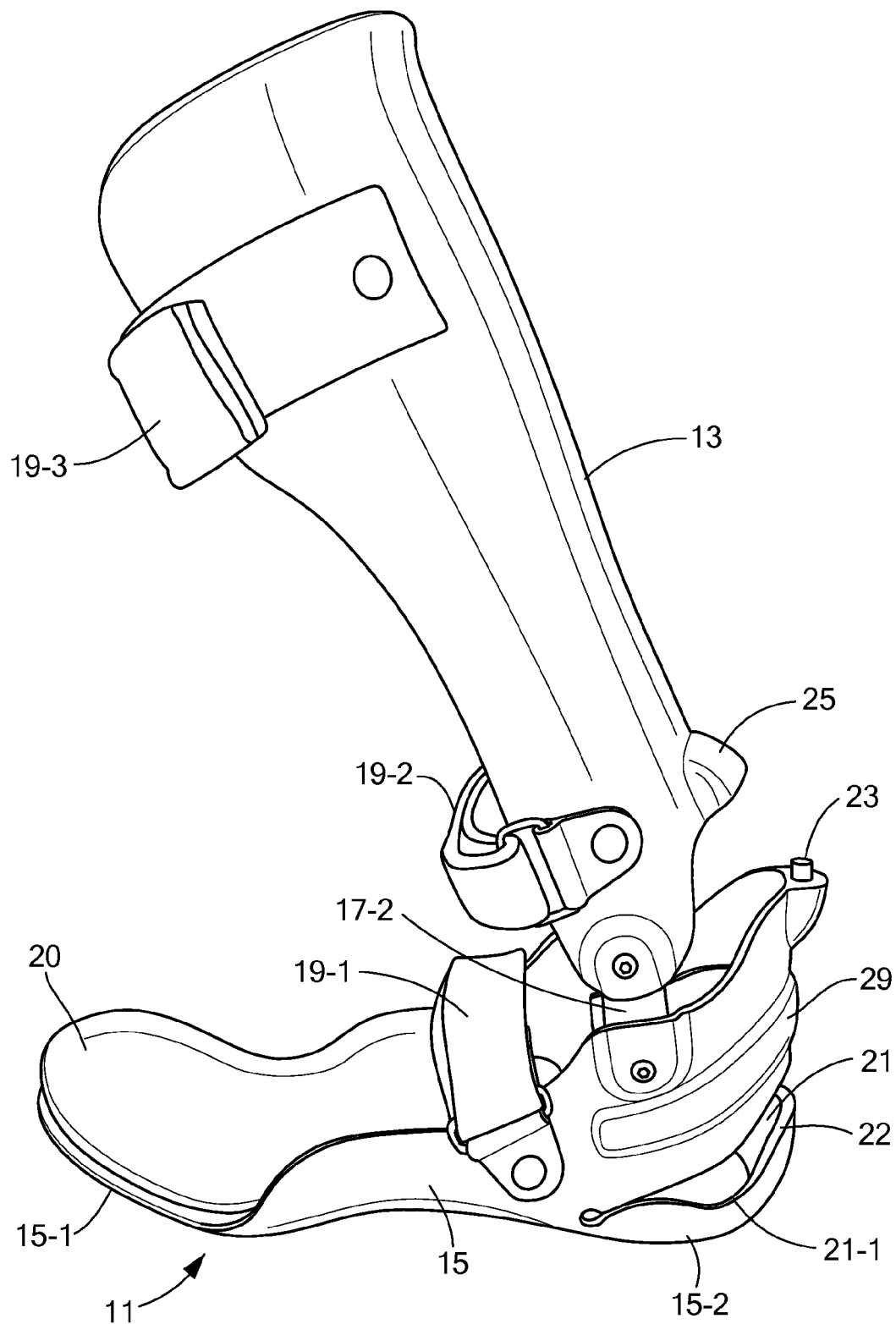
FIGS. 1(a)-(c) are right side perspective, front perspective and rear perspective views, respectively, of a first embodiment of an ankle-foot orthotic constructed according to the teachings of the present invention.
Figure 1B:
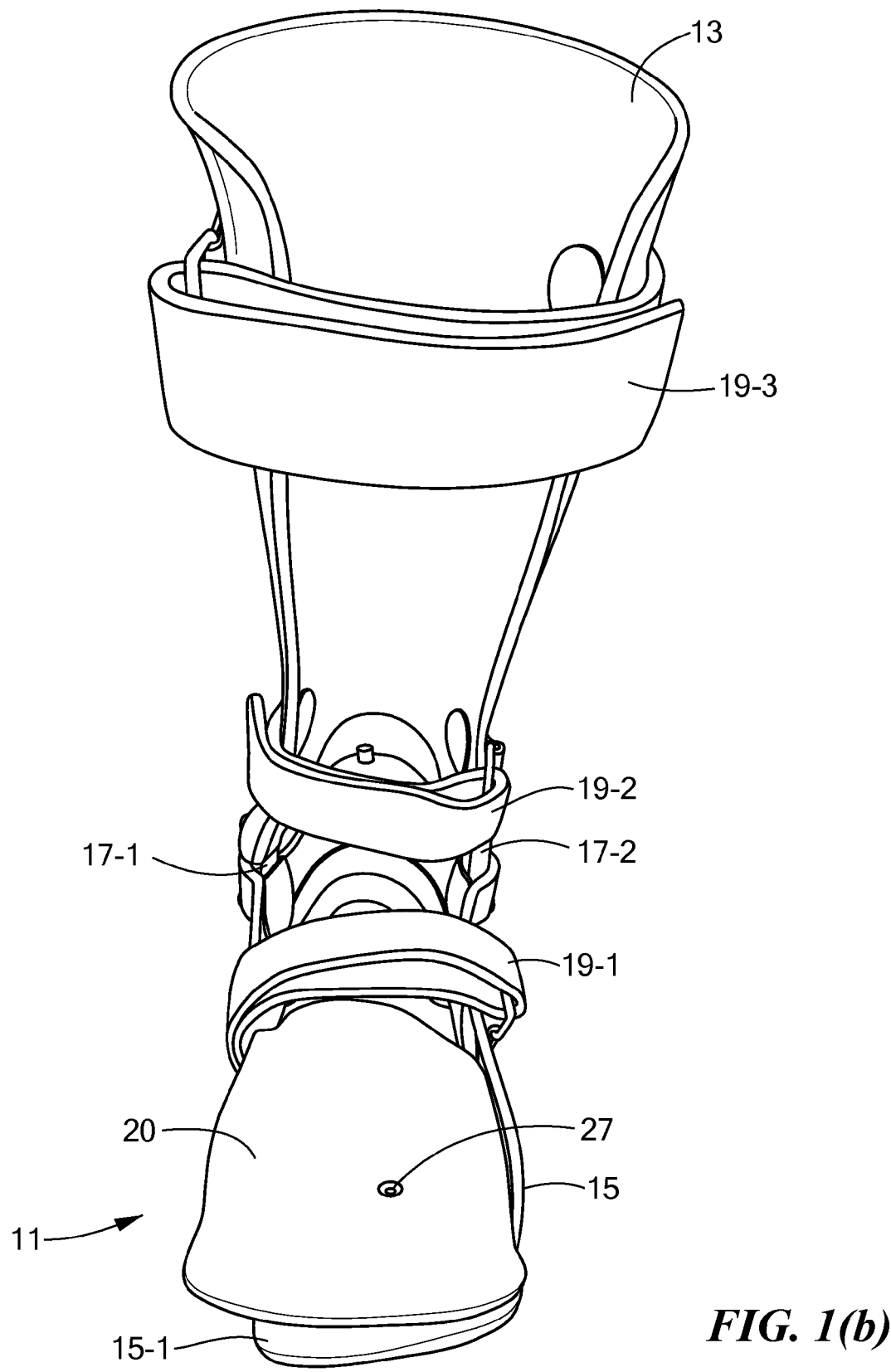

Referring now to the figures, there is a shown a first embodiment of an ankle-foot orthotic device that is constructed according to the teachings of the present invention, the orthotic device being identified generally by reference numeral 11. As will be described in detail below, orthotic device 11 is specifically designed to influence the rockers of the foot of a patient in order to induce a relatively smooth gait and a near normal stride length, which are principal objects of the present invention.

As seen most clearly in FIGS. 1(a)-2(b), orthotic device, or orthotic, 11 comprises an upper support member 13 that is designed to conform to the posterior aspect of the tibia of a patient, a lower support member 15 that is designed to conform to a portion of the foot and ankle of the patient, a pair of opposing dorsiflexion assist members 17 that pivotally join together members 13 and 15, a plurality of straps 19 for retaining upper and lower support members 13 and 15 onto the lower extremity of the patient, and a foot overlay 20 that is mounted onto lower support member 15 for reasons to become apparent below.

Upper support member 13 is constructed out of a rigid material, such as 3/16 inch thick polypropylene material. Preferably, upper support member 13 is constructed as a unitary, solid, generally C-shaped piece in transverse cross-section that is custom cast to closely conform to the majority of the posterior aspect of the tibia in order to maximize comfort and support.

Lower support member 15 is similarly constructed out of a rigid material, such as a 3/16 inch thick polypropylene material. As will be described in greater detail below, lower support member 15 is constructed as a unitary member that includes, among other things, a foot plate 15-1 that is custom cast to closely conform to the plantar aspect of the foot and a substantially enclosed cup 15-2 that is custom cast to closely conform to the medial, lateral, posterior and plantar aspects of the heel as well as the medial, lateral and posterior aspects of the ankle of the patient.

As a principal feature of the present invention, heel-ankle cup 15-2 of lower support member 15 is shaped to define a single, narrow, continuous slot 21 that is formed between the posterior region of the heel and the ankle of the patient and, in turn, extends forward in each of the medial and the lateral sides of the foot. As a feature of its design, slot 21 extends from the posterior region to both the medial and lateral sides along a gradual downward arc that, in addition, tapers inward in width (i.e. narrows), for reasons to become apparent below.

Figure 1C:
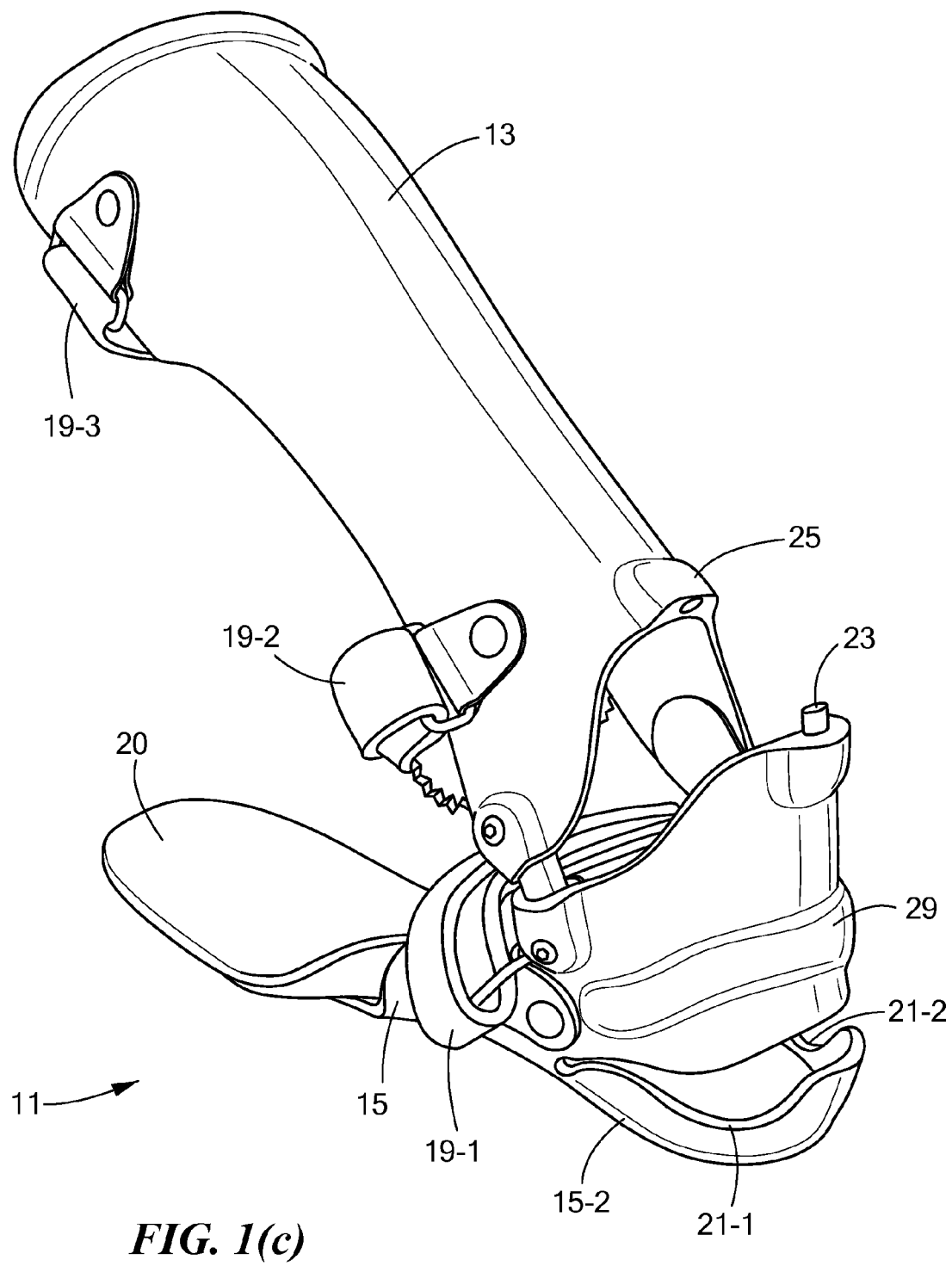
Figure 2A:
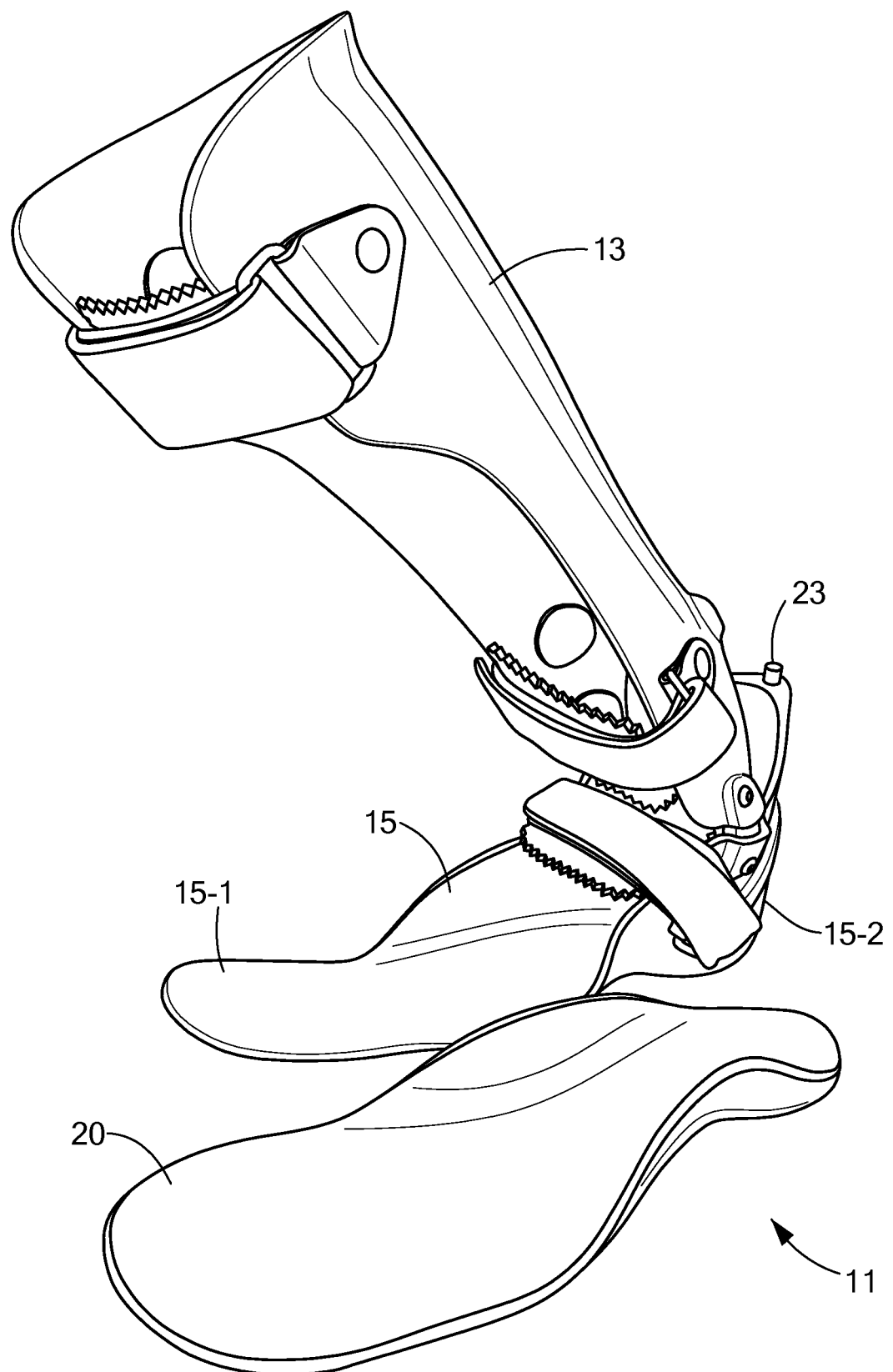
FIGS. 2(a)-(b) are partially exploded, right side perspective and rear perspective views, respectively, of the ankle-foot orthotic shown in FIG. 1(a)
Figure 2B:
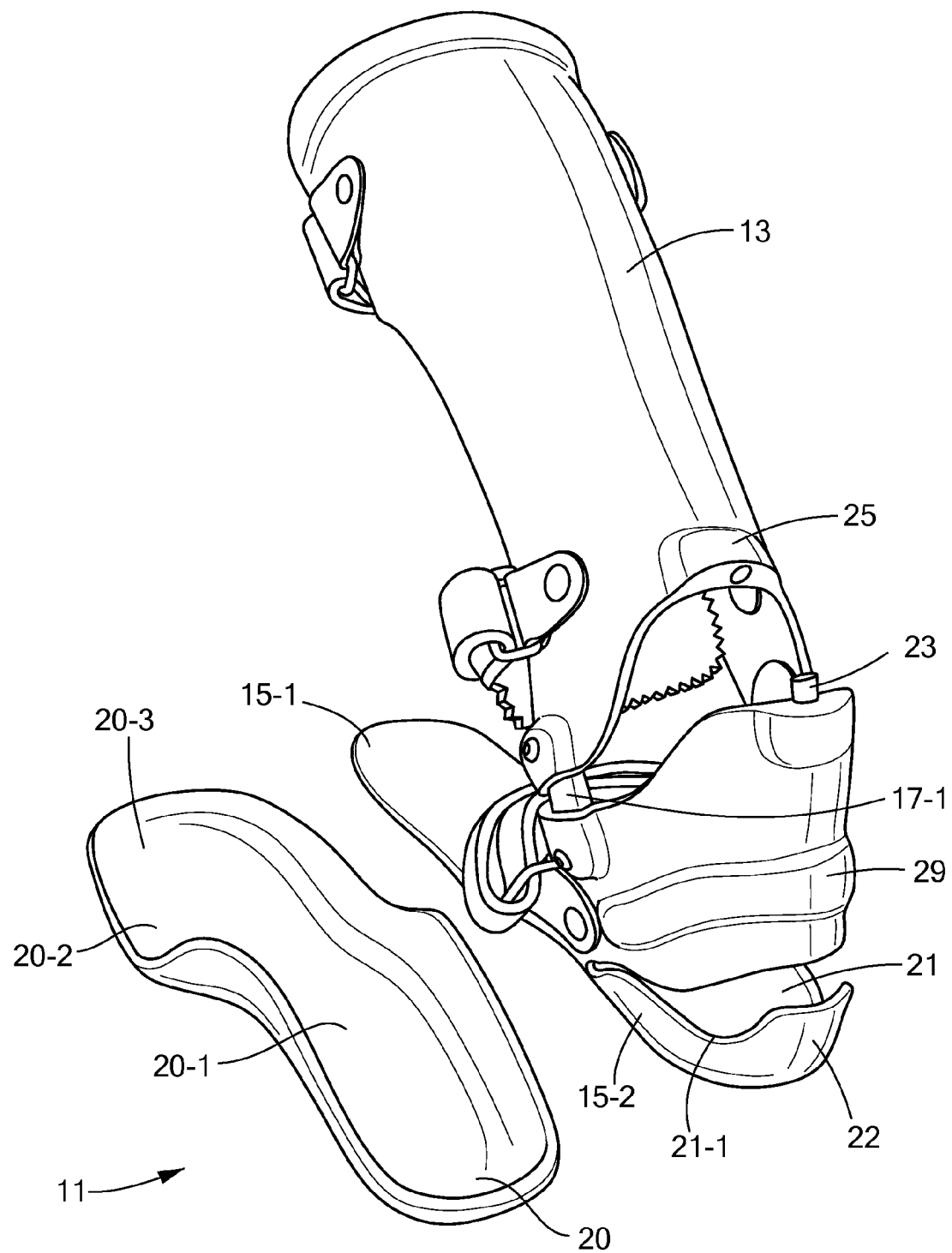

It should be noted that slot 21 includes a substantial downward curvature 21-1 on the medial side, as seen most clearly in FIGS. 1(a) and 2(c), as well as a substantially downward curvature 21-2 on the lateral side, as seen most clearly in FIG. 1(c). Together, curvatures 21-1 and 21-2 define a posterior heel raise 22 therebetween, raise 22 being designed to abut firmly against the inner surface of the heel counter of a shoe worn over orthotic 11 (i.e., for proper support and alignment of device 11 within the shoe).

As can be appreciated, the inclusion and particular design of slot 21 in lower support member 15 provides cup 15-2 in lower support member 15 with temporary heel compression capabilities (i.e., compressive movement, or drawing, of the two opposing pieces in the heel region on opposite sides of slot 21) upon the application of a suitable compressive force thereon, with cup 15-2 resiliently returning to its original configuration upon withdrawal of the compressive force. In particular, slot 21 preferably provides lower support member 15 with at least 5 degrees and, more specifically, in the range of approximately 5 degrees to 20 degrees of heel compression before contact is established between posterior heel raise 22 against the portion of heel-ankle cup 15-2 directly thereabove (i.e., on the direct opposite side of slot 21). As a consequence, the relatively rigid lower support member 15 allows for deceleration of plantar flexion while holding neutral subtaylor alignment in order to promote a soft, smooth heel roll. As a result, orthotic device 11 induces a smooth transition to midstance while allowing the normal 7-10 degrees of forefoot eversion, which is highly desirable.

In the absence of outside forces applied device 11, upper and lower support members 13 and 15 remain spaced slightly apart a generally uniform distance by assist members 17. As seen most clearly in FIGS. 1(a), 1(c) and 2(b), a generally cylindrical stop, or post, 23 is fittingly inserted into a corresponding vertical bore formed into the top, posterior region of lower support member 13. Stop 23 is dimensioned to extend vertically upward from lower support member 15 and contact the underside of an enlargement 25 formed on the bottom, posterior region of upper support member 15. In this capacity, post 23 functions as a plantar flexion stop that prevents lower leg hyperextension (i.e., overextended rearward displacement of the tibia relative to the foot) and, as such, serves as a principal feature of the present invention.

Stop 23 is preferably constructed using a high shock absorption material that is of a softer nature than either of members 13 and 15, such as a compressible silicone, for increased durability of device 11. In addition, it should be noted that the use of a silicone-like material for stop 23 renders device 11 suitably quiet during normal use, which is highly desirable.

Referring now to FIGS. 1(b), 1(c), 2(a) and 2(b), relatively flattened footplate 15-1 in lower support member 15 is adapted to support the treated foot of the patient. As noted briefly above, footplate 15-1 (as well as the remainder of lower support member 15) is preferably constructed of a relatively rigid material, such as a 3/16 inch thick polypropylene material. However, it should be noted that footplate 15-16 is not dimensioned to extend the full width of the foot of the patient. Rather, the midfoot and forefoot region of footplate 15-1 is narrowed so as to not directly support a portion of the medial region of the foot and, in particular, the first metatarsal bone, for reasons to become apparent below.

Foot overlay 20 is removably secured to the inner surface of footplate 15-1 by one or more rivets 27, as shown in FIG. 1(*b*). As can be seen, foot overlay 20 is dimensioned to extend the full width of the treated foot of the patient from forefoot to hindfoot. As a result, foot overlay 20 extends medially beyond footplate 15-1.

Foot overlay 20 is preferably constructed out of a more flexible material than footplate 15-1. For instance, foot overlay 20 is preferably manufactured of a reduced thickness plastic, such as a 3/32 inch thick polypropylene, foam, or other suitable comfortable and flexible material. Because foot overlay 20 (i) is constructed of a more flexible material than footplate 15-1 and (ii) extends medially beyond footplate 15-1, the first metatarsal of the patient is provided with less rigid support in relation to the remainder of the treated foot. As a result, device 11 promotes more natural and proper pronation (i.e., medial to lateral roll of the midfoot into midstance), which is a principal object of the present invention. By comparison, a brace that applies uniform rigidity and support to the entire plantar region of a treated foot prevents adequate medial-lateral midfoot roll and, as a consequence, causes the foot to supernate (i.e., roll outward), which is highly undesirable.

In the present embodiment, foot overlay 20 is additionally shaped to include, among other things, (i) an intrinsic sustentaculum pressure portion 20-1 just before midstance in order to control excessive pronation (inward roll of foot), (ii) an intrinsic, full flexible portion 20-2 that assists in the deceleration of the progression of the tibia during forefoot rocker contact (as gastroc and soleus muscles contract), and (iii) a terminal stance up sweep portion 20-3 to assist toe push off, thereby completing the weight bearing cycle for the involved limb.

In addition, a carbon fiber band 29 is preferably secured to lower support member 15 and wraps around the ankle from the medial side to the lateral side. As can be appreciated, carbon fiber band 29 provides additional rigidity and support to the ankle region of lower support member 15.

As noted above, first and second dorsiflexion assist members 17-1 and 17-2 pivotally join the medial and lateral sides, respectively, of upper and lower support members 13 and 15. Each dorsiflexion assist member 17 is preferably constructed as an 85 durometer strut that is pivotally coupled at each end to upper and lower support members 13 and 15. In use, opposing dorsiflexion assist members 17 enable upper member 13 to smoothly pivot forward relative to lower support member 15 as body weight progresses forward during the stance phase. Once weight is lifted from the limb upon toe-off (i.e., after the limb raises off the floor), resilient assist members 17 promptly induce dorsiflexion (i.e., members 17 pull the top of the foot back towards the tibia and in proper position for a subsequent heel strike), with stop 23 silently abutting enlargement 25 to prevent hyperextension.

Figure 3A:
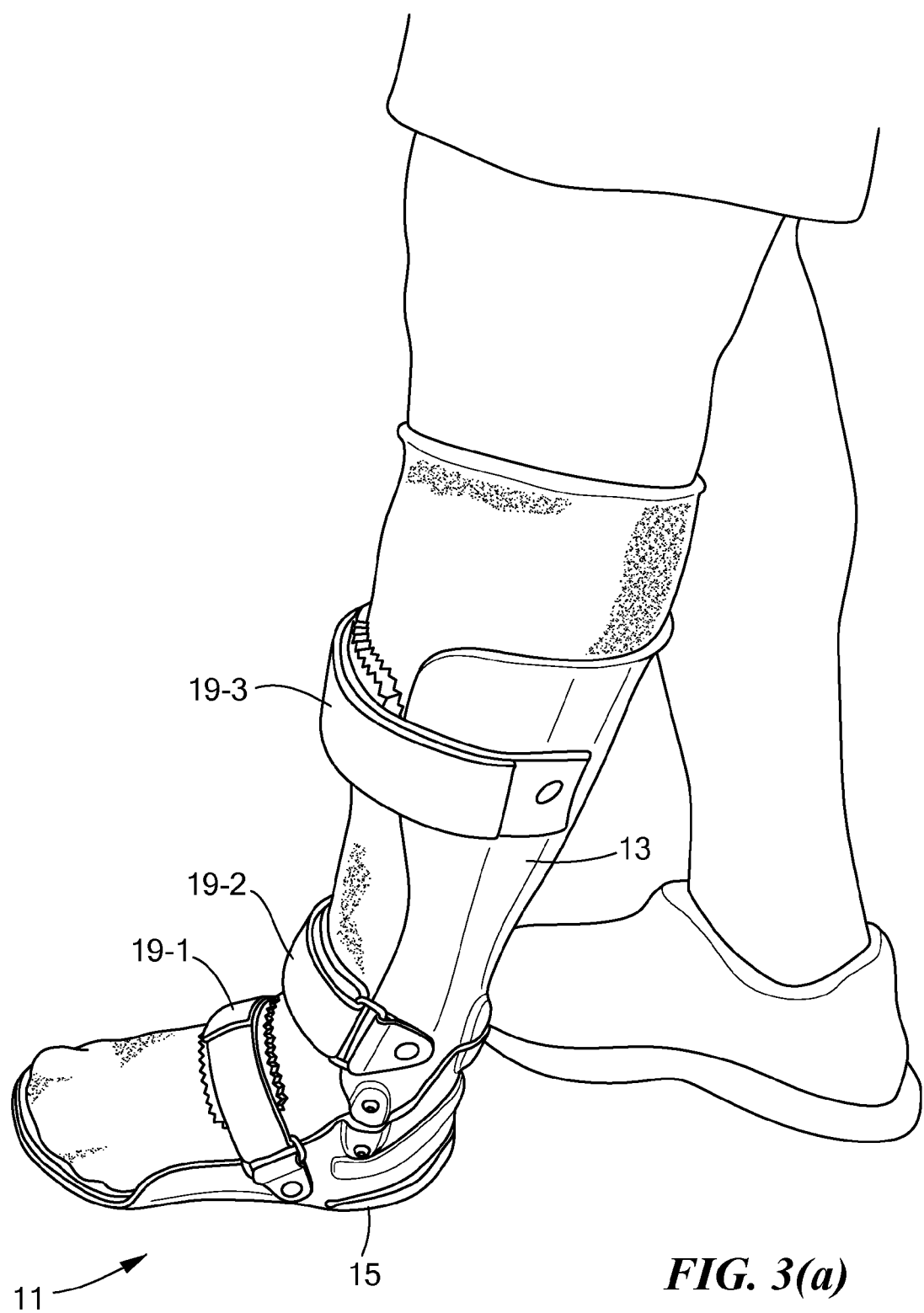
FIGS. 3(a)-(b) are right side perspective views of the ankle-foot orthotic shown in FIG. 1(a) at selected stages of the stance phase of the gait cycle, the orthotic being shown wore by a patient for ease of illustration.
Figure 3B:
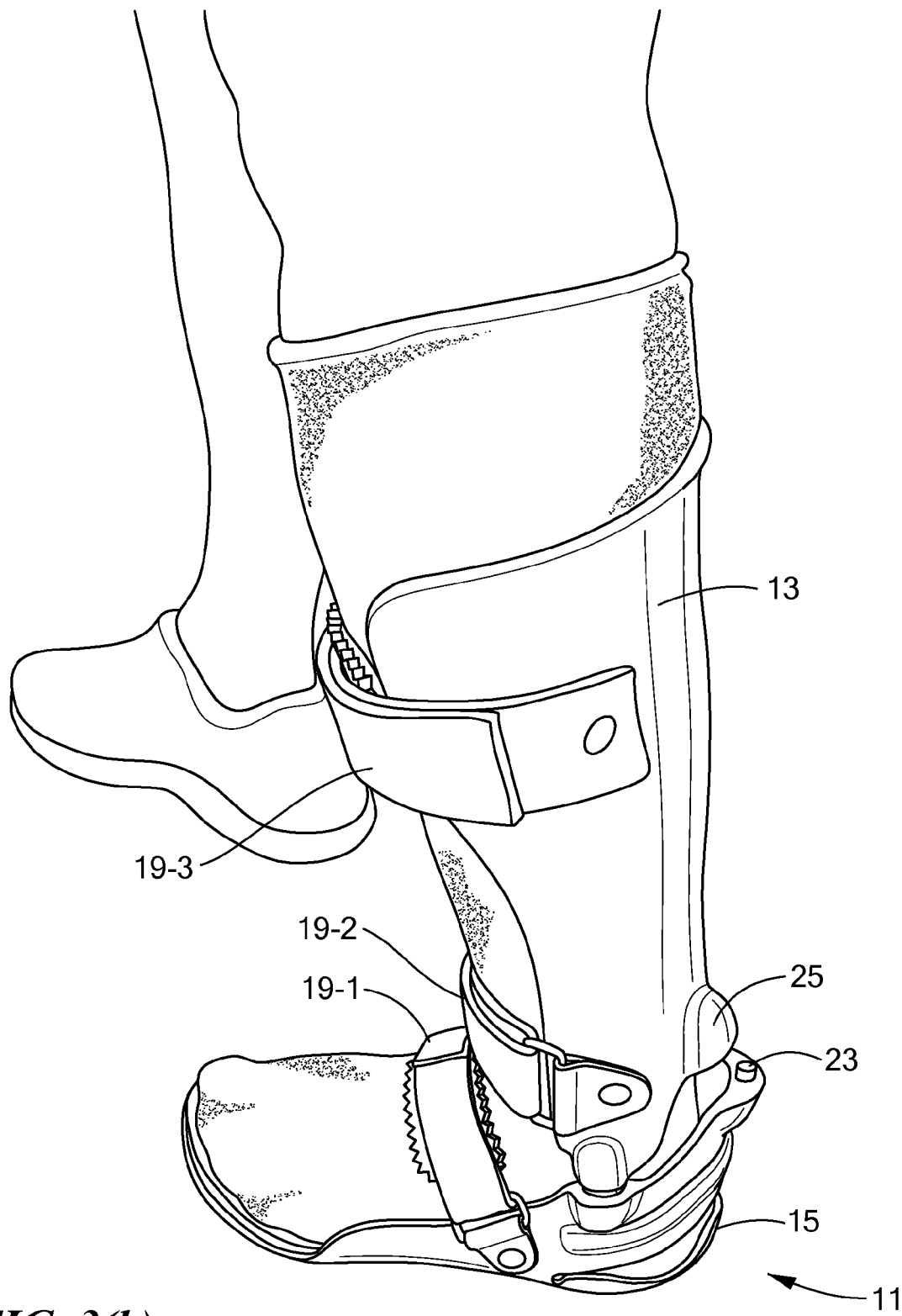

As referenced briefly above, a plurality of releasably securable, adjustable straps 19 is provided to retain upper and lower support members 13 and 15 onto the lower extremity of the patient, as shown in FIGS. 3(*a*)-(*b*). Specifically, device 11 includes (i) a releasably securable, adjustable instep strap 19-1 that is coupled at opposite ends to the medial and lateral sides of the midfoot region of lower support member 15, instep strap 19-1 assisting with heel seat and preventing heel migration rise during the heel off stage of the gait cycle, (ii) a releasably securable, adjustable distal talar strap 19-2 that is coupled at opposite ends to the medial and lateral sides of the talus region of the upper support member 13, strap 19-2 preventing excessive tibia progression while, at the same time, allowing the talus to slide anterior on the calcaneus during plantar flexing, adducting and everting (this motion causing internal rotation of the lower leg which enables weight bearing forces to be properly absorbed), and (iii) a releasably securable, adjustable distal tibia strap 19-3 that is coupled at opposite ends to the medial and lateral sides of the distal end of upper support member 13.

Each strap 19 is represented herein is being constructed out of a soft and highly comfortable material, such as foam or a thin, flexible plastic, that is in turn provided with separate hook and pile strips on opposing ends of the same surface. Accordingly, by feeding each strap 19 through an enclosed bracket which, in turn, is secured to either member 13 or 15 by rivets, straps 19 can be double backed and secured in place to retain device 11 on the lower extremity of the patient.

The embodiment shown above is intended to be merely exemplary and those skilled in the art shall be able to make numerous variations and modifications to it without departing from the spirit of the present invention. All such variations and modifications are intended to be within the scope of the present invention as defined in the appended claims.

Figure 4A:
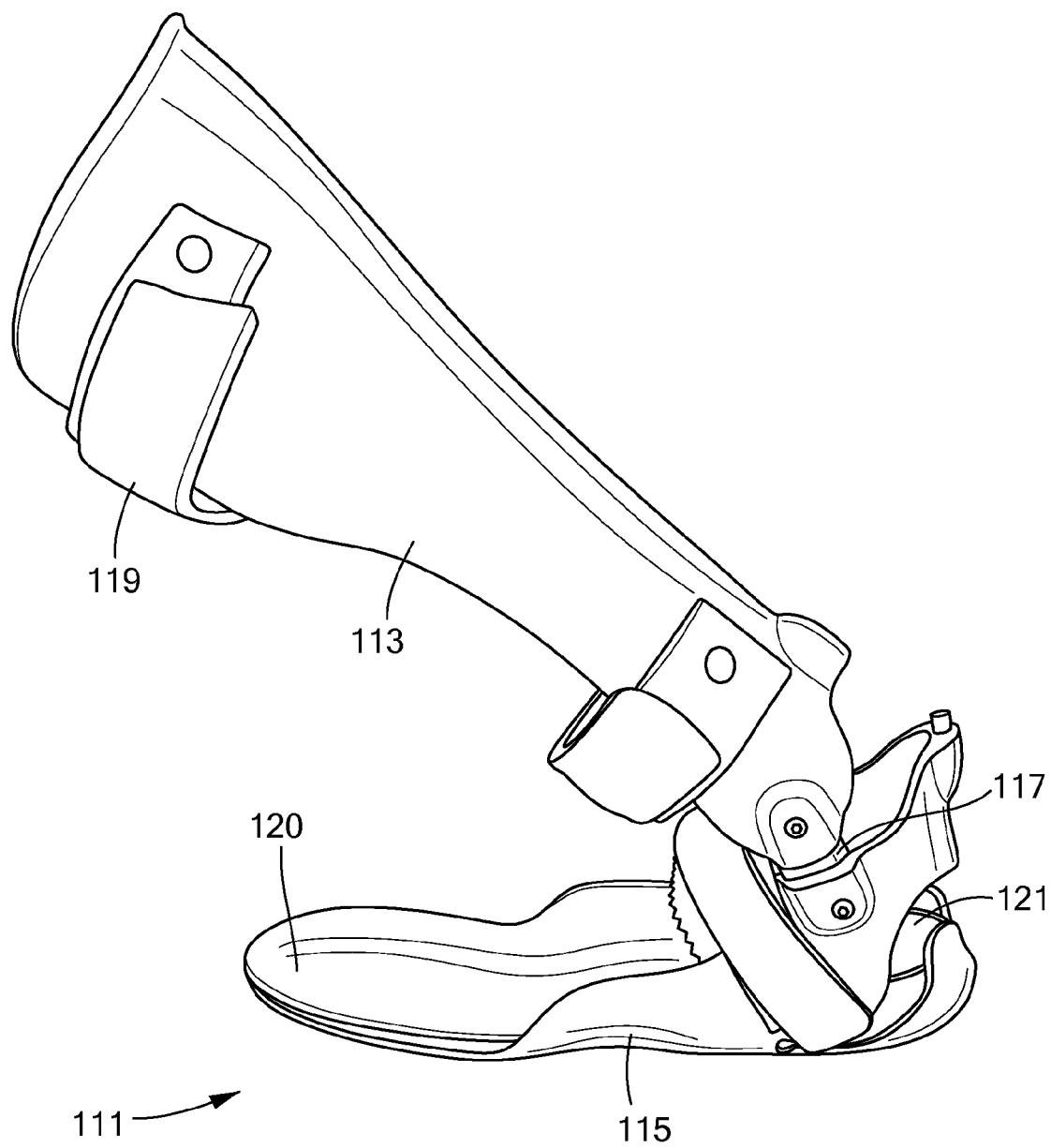
FIGS. 4(a)-(b) are right side perspective and enlarged, rear perspective views, respectively, of a second embodiment of an ankle-foot orthotic constructed according to the teachings of the present invention.
Figure 4B:
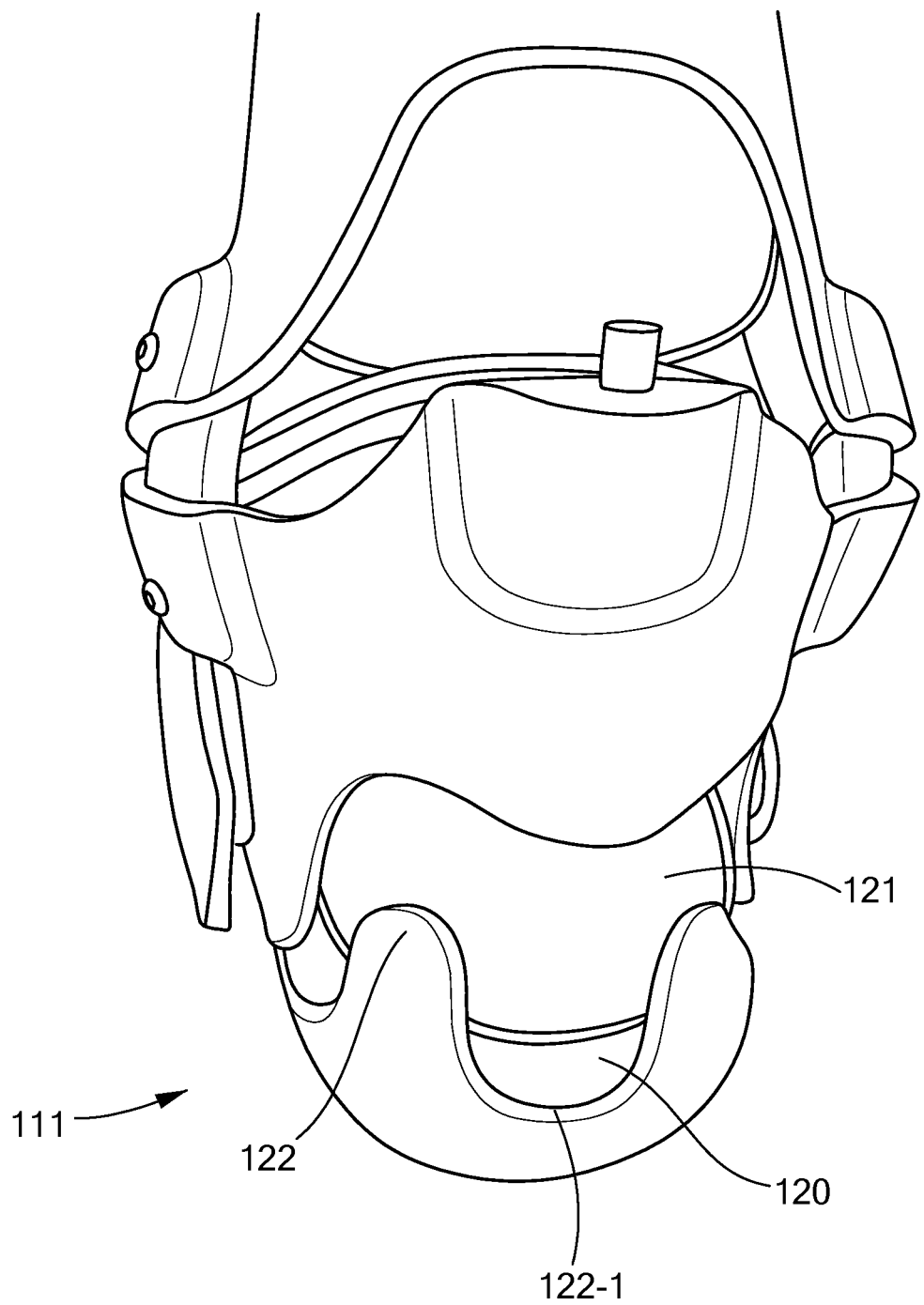

For instance, referring now to FIG. 4(*a*), there is shown a second embodiment of an ankle-foot orthotic device that is constructed according to the teachings of the present invention, the orthotic device being identified generally by reference numeral 111. As can be seen device 111 is similar to device 11 in that device 111 comprises an upper support member 113 that is designed to conform to the posterior aspect of the tibia of a patient, a lower support member 115 that is designed to conform to a portion of the foot and ankle of the patient, a pair of opposing dorsiflexion assist members 117 that pivotally join together members 113 and 115, a plurality of straps 119 for retaining upper and lower support members 113 and 115 onto the lower extremity of the patient, and a removable foot overlay 120 that is mounted onto lower support member 115 to promote proper pronation into midstance.

Device 111 differs slightly from device 11 in a few notable ways. As a first distinction, device 111 includes a heel compression slot 121 in lower support member 115 that, although in similar in function to slot 21 in lower support member 15, is slightly different in shape. In particular, as seen most clearly in FIG. 4(*b*), slot 121 defines a posterior heel raise 122 that is shaped, or cut-out, to include a posterior recession, or central dip, 122-1. As can be seen, dip 122-1 extends below the posterior heel portion of highly flexible foot overlay 120. Accordingly, the inclusion of posterior recession 122-1 allows for the majority of heel of the patient to expand and project through dip 122-1 at initial heel strike. Because the heel of the patient is limited to contact against the posterior heel portion of flexible foot overlay 120, there is limited rubbing or other similar contact of the heel against the relatively rigid heel raise 122 during normal use, which can otherwise result in blistering and/or other discomfort to the patient.

As a second distinction, device 111 is constructed without the use a carbon fiber band in the dorsal ankle region of lower support member 115 (e.g., band 29 in device 11). As can be appreciated, it has been found that the rigidity of lower support member 115 within the ankle region may be of a sufficient level so as not to require additional stiffening members.

Figure 5:
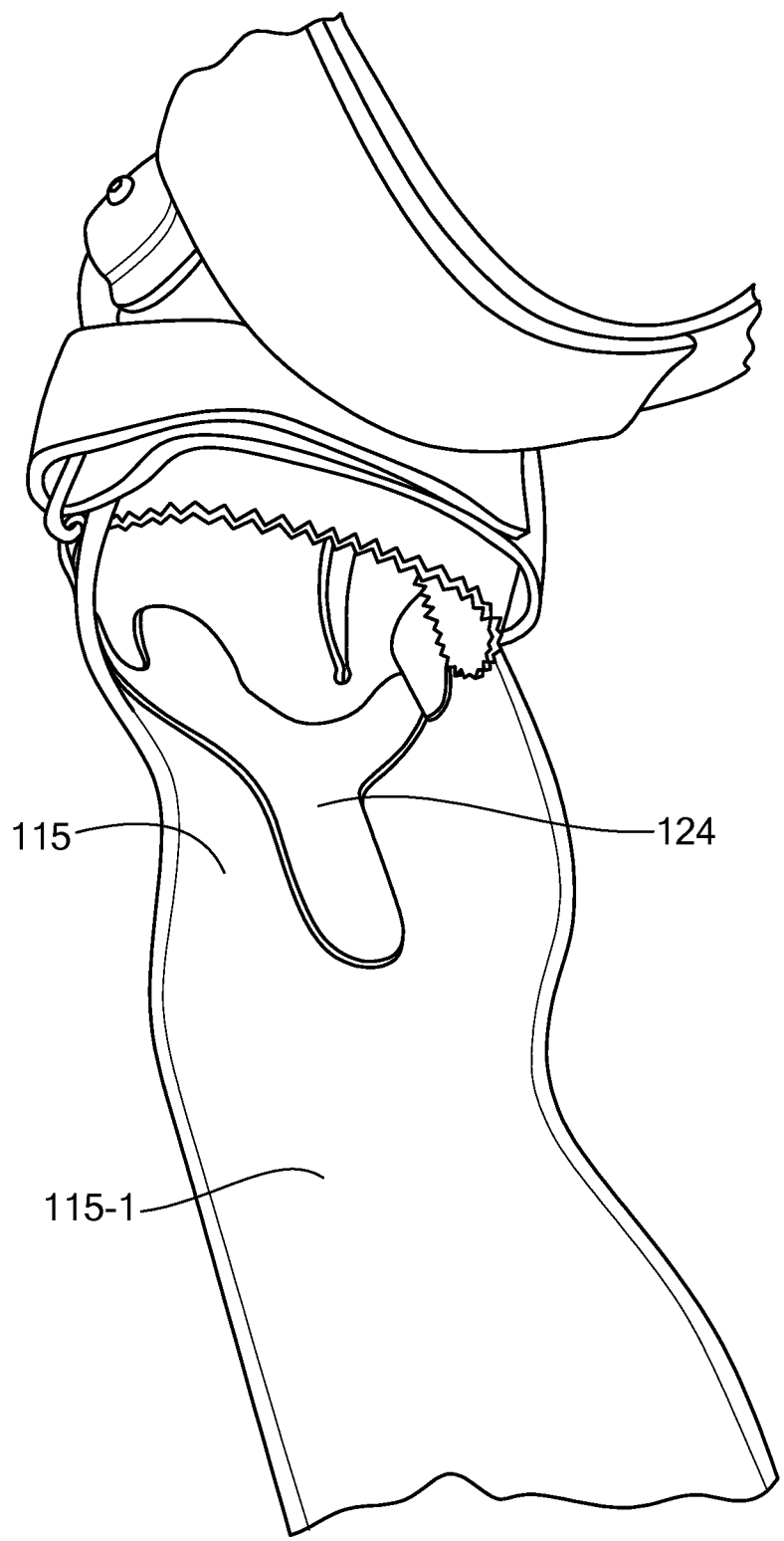
FIG. 5 is an enlarged front perspective of the ankle-foot orthotic shown in FIG. 4(a), the orthotic being shown with the foot overlay removed therefrom for purposes of clarity.

As a third distinction, device 111 is provided with a shank 124 for stiffening footplate 115-1 in lower support member 115. Specifically, as shown in FIG. 5, a T-shaped shank, or stiffening insert, 124, which is constructed of a suitably rigid material (e.g., a 3/32 inch thick polypropylene material) is vacuum formed into the top surface of footplate 115-1 in the hindfoot region. With insert 124 disposed between footplate 115-16 and foot overlay 120, rivets (not shown) are driven therethrough to maintain assembly. In use, insert 124 provides selective rigidity to footplate 115-1 and serves, most importantly, to promote a smoothing out of the first and second rockers of the foot during the gait cycle.

What is claimed is:

1. An orthotic for treating a lower extremity of a patient, the lower extremity comprising a tibial portion, an ankle portion, a heel portion and a foot portion, the orthotic comprising:
   (a) an upper support member adapted to conform to the tibial portion;
   (b) a lower support member adapted to conform to the foot, heel and ankle of the patient, the lower support member being pivotally coupled to the upper support member, the lower support member including a footplate for supporting the foot portion of the patient; and
   (c) a foot overlay mounted onto the footplate of the lower support member, the foot overlay being larger in width than the footplate of the lower support member;
   (d) wherein the lower support member comprises a rigid cup for receiving the heel and ankle portions of the lower extremity, the cup being shaped to define a slot that enables the cup to compress upon the application of a suitable compressive force thereto.

2. The orthotic as claimed in claim 1 wherein the foot overlay extends beyond the footplate of the lower support member in the medial aspect.

3. The orthotic as claimed in claim 2 wherein the foot overlay is constructed of a more flexible material than the footplate of the lower support member.

4. The orthotic as claimed in claim 3 further comprising a stiffening insert disposed between the footplate and the foot overlay.

* * * * *